US006455749B1

(12) United States Patent
Vaughn

(10) Patent No.: US 6,455,749 B1
(45) Date of Patent: *Sep. 24, 2002

(54) METHOD FOR INCREASING LIGHT OLEFIN YIELD BY CONVERSION OF A HEAVY HYDROCARBON FRACTION OF A PRODUCT TO LIGHT OLEFINS

(75) Inventor: Stephen Neil Vaughn, Kingwood, TX (US)

(73) Assignee: ExxonMobil Chemical Patents, Inc., Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/943,399

(22) Filed: Oct. 3, 1997

(51) Int. Cl.$^7$ .............................. C07C 1/00; C07C 1/20
(52) U.S. Cl. ................. 585/640; 585/638; 585/639; 585/324
(58) Field of Search ................. 585/638, 639, 585/640, 324

(56) References Cited

U.S. PATENT DOCUMENTS

| | | | |
|---|---|---|---|
| 4,071,573 A | 1/1978 | Owen et al. | 260/668 |
| 4,138,440 A | 2/1979 | Chang et al. | 260/668 |
| 4,338,475 A | 7/1982 | Pennington et al. | 585/408 |
| 4,396,789 A | 8/1983 | Barrocas et al. | 585/639 |
| 4,423,274 A | 12/1983 | Daviduk et al. | 585/640 |
| 4,433,188 A | 2/1984 | Hoelderich et al. | 585/640 |
| 4,440,871 A | 4/1984 | Lok et al. | 502/214 |
| 4,527,001 A | 7/1985 | Kaiser | 585/643 |
| 4,547,616 A | 10/1985 | Avidan et al. | 585/640 |
| 4,579,999 A * | 4/1986 | Dould et al. | 585/640 |
| 4,590,320 A | 5/1986 | Sapre | 585/324 |
| 4,677,243 A * | 6/1987 | Kaiser | 585/638 |
| 4,752,651 A | 6/1988 | Kaiser | 585/640 |
| 4,861,938 A | 8/1989 | Lewis et al. | 585/640 |
| 4,873,390 A | 10/1989 | Lewis et al. | 585/638 |
| 4,973,792 A | 11/1990 | Lewis et al. | 585/638 |
| 5,028,400 A | 7/1991 | Harandi et al. | 422/211 |
| 5,157,181 A | 10/1992 | Stine et al. | 585/329 |
| 5,177,283 A | 1/1993 | Ward | 585/446 |
| 5,744,680 A | 4/1998 | Mulvaney, III et al. | 585/640 |
| 5,914,433 A | 6/1999 | Marker | 585/313 |

FOREIGN PATENT DOCUMENTS

| | | |
|---|---|---|
| CA | 1 130 820 | 8/1982 |
| CA | 1 196 031 | 10/1985 |
| DE | 3 524 890 | 7/1985 |
| DE | 3524890 * | 1/1986 |
| EP | 088 965 | 9/1983 |
| EP | 0 882 692 A1 | 12/1998 |
| GB | 2171718 * | 9/1986 |
| GB | 2 171 718 A | 9/1986 |
| WO | WO 86/04577 | 8/1986 |

OTHER PUBLICATIONS

Zeolites, vol. 17, pp. 212–222 (1996).

* cited by examiner

Primary Examiner—Walter D. Griffin
(74) Attorney, Agent, or Firm—Paul T. LaVoie

(57) ABSTRACT

A method for increasing light olefin yield during conversion of oxygenates to olefins comprising: contacting an oxygenate feed in a primary reactor with a non-zeolitic molecular sieve catalyst under conditions effective to produce a first product comprising light olefins; separating the first product into light olefins and a heavy hydrocarbon fraction; feeding the heavy hydrocarbon fraction either back into the primary reactor or to a separate auxiliary reactor; and, subjecting the heavy hydrocarbon fraction to conditions effective to convert at least a portion of the heavy hydrocarbons to light olefins.

36 Claims, No Drawings

METHOD FOR INCREASING LIGHT OLEFIN YIELD BY CONVERSION OF A HEAVY HYDROCARBON FRACTION OF A PRODUCT TO LIGHT OLEFINS

FIELD OF THE INVENTION

The present invention is directed to a method for increasing the yield of light olefins during the conversion of oxygenates to olefins by converting heavy hydrocarbons in the product to light olefins either by (a) recycling the heavy hydrocarbons to the primary reactor after removing the light olefins, or (b) converting the heavy hydrocarbons to light olefins in a separate auxiliary reactor.

BACKGROUND OF THE INVENTION

Light olefins (defined herein as "ethylene and propylene") serve as feeds for the production of numerous chemicals. Light olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

Because light olefins are the most sought after products of such a reaction, a continuing need exists for new methods to increase the yield of light olefin products and reduce the yield of unwanted products, such as "heavy" hydrocarbons having molecular weights heavier than propane.

SUMMARY OF THE INVENTION

The present invention provides a method for increasing light olefin yield during conversion of oxygenates to olefins. The method comprises: contacting an oxygenate feed in a primary reactor with a non-zeolitic molecular sieve catalyst under first conditions effective to produce a first product comprising light olefins; separating the first product into light olefins and a heavy hydrocarbon fraction; feeding the heavy hydrocarbon fraction either back to the primary reactor or to a separate auxiliary reactor; and, subjecting the heavy hydrocarbon fraction to second conditions effective to convert at least a portion of the heavy hydrocarbons to light olefins.

DETAILED DESCRIPTION OF THE INVENTION

In the conversion of oxygenates to light olefins (defined herein as ethylene and propylene), it is desirable to maximize the yield of light olefins. The present invention maximizes the yield of light olefins by converting the "heavy hydrocarbon fraction" of the reaction product to olefins. The "heavy hydrocarbon fraction" is defined herein as the fraction containing hydrocarbons having a molecular weight greater than propane. The conversion of heavy hydrocarbons to light olefins is accomplished either by (a) returning all or a part of the heavy hydrocarbon fraction to the primary reactor, where the heavy hydrocarbons are converted to light olefins along with additional oxygenate feed, or (b) conveying the heavy hydrocarbon fraction to a separate auxiliary reactor where the heavy hydrocarbons are converted to light olefins.

Molecular sieve catalysts that are suitable for use in the primary reactor are non-zeolitic catalysts, which include, but are not necessarily limited to silicoaluminophosphates ("SAPO's"). SAPO's have a three-dimensional microporous crystal framework of $PO_2^+$, $AlO_2^-$, and $SiO_2$ tetrahedral units. Preferred SAPO's for use in the primary reactor are "small" and "medium" pore SAPO's. "Small pore" molecular sieve catalysts are defined as catalysts with pores having a diameter of less than about 5.0 Angstroms. "Medium pore" molecular sieve catalysts are defined as catalysts with pores having a diameter in the range of from about 5 to about 10 Angstroms.

Suitable SAPO's for use in the invention include, but are not necessarily limited to SAPO-11, SAPO-44, SAPO-34, SAPO-17, and SAPO-18. A preferred SAPO is SAPO-34, which may be synthesized according to U.S. Pat. No. 4,440,871, incorporated herein by reference, and Zeolites, Vol. 17, pp. 512–522 (1996), incorporated herein by reference.

SAPO's with added substituents also may be useful in the present invention. These substituted SAPO's form a class of molecular sieves known as "MeAPSO's." Suitable substituents include, but are not necessarily limited to nickel, cobalt, strontium, barium, and calcium.

Any molecular sieve catalyst capable of converting hydrocarbons with 4 or more carbon atoms into light olefins may be used in an auxiliary reactor. Preferred molecular sieve catalysts for the auxiliary reactor are zeolites.

Structural types of zeolites that are suitable for use in the auxiliary reactor with varying levels of effectiveness include, but are not necessarily limited to AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO and substituted examples of these structural types, as described in W. M. Meier and D. H. Olsen, Atlas of Zeolite Structural Types (Butterworth Heineman-3rd ed. 1997), incorporated herein by reference. Structural types of medium pore molecular sieves useful in the present invention include, but are not necessarily limited to, MFI, MEL, MTW, EUO, MTT, HEU, FER, AFO, AEL, TON, and substituted examples of these structural types, as described in the Atlas of Zeolite Types, previously incorporated herein by reference. A preferred zeolite for the auxiliary reactor is ZSM-5.

The process for converting oxygenates to olefins employs an organic starting material (feedstock) preferably comprising "oxygenates." As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety preferably should contain in the range of from about 1 to about 10 carbon atoms and more preferably in the range of from about 1 to about 4 carbon atoms. Representative oxygenates include, but are not necessarily limited to, lower straight chain or branched aliphatic alcohols, their unsaturated counterparts, and their nitrogen, halogen and sulfur analogues. Examples of suitable compounds include, but are not necessarily limited to: methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; n-alkyl amines, n-alkyl halides, n-alkyl sulfides having n-alkyl groups of comprising the range of from about 3 to about 10 carbon atoms; and mixtures thereof. As used herein, the term "oxygenate" designates only the organic material used as the feed. The total charge of feed to the reaction zone may contain additional compounds such as diluents.

Preferably, the oxygenate feedstock should be fed to the primary reactor and contacted in the vapor phase in a reaction zone with the selected molecular sieve catalyst at effective process conditions so as to produce the desired olefins, i.e., an effective temperature, pressure, WHSV (Weight Hourly Space Velocity) and, optionally, an effective amount of diluent, correlated to produce olefins. Alternately, the process may be carried out in a liquid or a mixed vapor/liquid phase. When the process is carried out in the liquid phase or a mixed vapor/liquid phase, different conversions and selectivities of feedstock-to-product may result depending upon the catalyst and reaction conditions.

The temperature employed in the primary reaction zone may vary over a wide range depending, at least in part, on the selected catalyst. Although not limited to a particular temperature, best results will be obtained if the process is conducted at temperatures in the range of from about 200° C. to about 700° C., preferably in the range of from about 250° C. to about 600° C., and most preferably in the range of from about 300° C. to about 500° C. Lower temperatures generally result in lower rates of reaction, and the formation of the desired light olefin products may become markedly slow. However, at higher temperatures, the process may not form an optimum amount of light olefin products, and the coking rate may become too high.

When an auxiliary reactor is used, the temperature range may be optimized to more effectively convert $C_4^+$ hydrocarbons to light olefins. Although not limited to a particular temperature, best results will be obtained if the process is conducted at temperatures within the range of from about 300° C. to about 750° C., preferably in the range of from about 450° C. to about 700° C. Lower temperatures generally result in lower rates of reaction and the formation of desired lower olefins may become markedly slow. However, at higher temperatures, the process may not form an optimum amount of light olefin products and the coking rate may become too high.

Light olefin products will form in both the primary reaction zone and in the optional auxiliary reactor—although not necessarily in optimum amounts—at a wide range of pressures, including but not limited to autogeneous pressures and pressures in the range of from about 0.1 kPa to about 100 MPa. A preferred pressure is in the range of from about 6.9 kPa to about 34 MPa, most preferably in the range of from about 48 kPa to about 0.34 MPa. The foregoing pressures are exclusive of diluent, if any is present, and refer to the partial pressure of the feedstock as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction cycle time may vary from tenths of seconds to a number of hours. The reaction cycle time is largely determined by the reaction temperature, the pressure, the catalyst selected, the weight hourly space velocity, the phase (liquid or vapor), and the selected process design characteristics.

A wide range of weight hourly space velocities (WHSV), defined as weight feed per hour per weight of catalyst, for the feedstock will function in the present invention. The WHSV generally should be in the range of from about 0.01 $hr^{-1}$ to about 5000 $hr^{-1}$, preferably in the range of from about 1.0 $hr^{-1}$ to about 2000 $hr^{-1}$, and most preferably in the range of from about 20 $hr^{-1}$ to about 1000 $hr^{-1}$. The catalyst may contain other materials which act as inerts, fillers, or binders; therefore, the WHSV is calculated on the feed rate of oxygenate and recycle hydrocarbons and weight of inert, filler, and binder free catalyst.

When an auxiliary reactor is used, a wide range of WHSV's may be used in the secondary conversion reactor. The WHSV generally should be in the range of from about 0.1 $hr^{-1}$ to about 5000 $hr^{-1}$ preferably in the range of from about 1.0 $hr^{-1}$ to about 1000 $hr^{-1}$, and most preferably in the range of from about 1.0 $hr^{-1}$ to about 100 $hr^{-1}$. The catalyst may contain other materials which act as inerts, fillers, or binders; therefore, the WHSV is calculated on the basis of feed rate of hydrocarbon and weight of inert, filler, and binder free catalyst.

One or more diluents may be fed to the reaction zone with the oxygenates, such that the total feed mixture comprises diluent in a range of from about 1 mol % and about 99 mol %. Diluents which may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Preferred diluents are water and nitrogen.

The ethylene and propylene may be separated from the remainder of the product stream, including the heavy hydrocarbon fraction, using any suitable known means, preferably cryogenically. In one embodiment of the invention, the heavy hydrocarbon fraction (or heavy hydrocarbons separated from the heavy hydrocarbon fraction) is recycled back to the primary reactor along with additional oxygenate feed. The recycled heavy hydrocarbon stream may be reintroduced into the primary reactor in numerous ways, including but not limited to, mixing with a regenerated catalyst stream between a regenerator and the primary reactor and before addition of the oxygenated feed, and mixing with the oxygenate feed and the blend of oxygenate and hydrocarbon feed to the primary reactor in either single or multiple locations along the reaction vessel. The same cycle may be repeated until no net $C_4^+$ products are produced, or until only a desired amount of $C_4^+$ product remains. This embodiment has the advantage that the exothermic conversion of oxygenate to olefins is counteracted to some extent by the endothermic $C_4^+$ cracking reactions.

In a second embodiment, the heavy hydrocarbon feed is cycled to a separate auxiliary reactor in which process conditions and catalyst are selected to optimize the production of light olefins from heavy hydrocarbons. Although not intending to limit the invention, preferred catalysts for use in the auxiliary reactor are zeolites, most preferably ZSM-5. By using a separate auxiliary reactor, an optimized oxygenate to olefins catalyst can be used to catalyze the conversion of oxygenates to light olefins in a first reaction zone, a second catalyst can be used to catalyze the conversion of $C_4^+$ hydrocarbons to light olefins in a second reaction zone, and both reactors can be optimized in sizing and process condition for the desired reactions to occur.

It may be desirable to provide for $C_4^+$ product purge at some point in the cycle to provide a ready source of fuel gas for plant use, $C_4^+$ product for sale, or to limit the size of the recycle stream to the primary reactor.

A preferred embodiment for the primary reactor is a circulating fluid bed or riser reactor with continuous regeneration, similar to a modern fluid catalytic cracker. Fixed bed reactors are not practical for use in the primary reactor because oxygenate to olefin conversion is highly exothermic and requires several stages with intercoolers or other cooling devices. The reaction also results in a high pressure drop due to the production of low pressure, low density gas.

Preferred auxiliary reactors include fluid bed, fixed bed, or fired tube reactors. The $C_4^+$ cracking process is endothermic; therefore, the reactor should be adapted to supply heat as necessary to maintain a suitable reaction temperature. On-line or periodic regeneration of the catalyst may be provided by any suitable means known in the art.

The invention will be better understood with reference to the following examples which are intended to illustrate, but not to limit the present invention.

EXAMPLE I

A sample of 50.7 mg of SAPO-34 catalyst obtained from UOP, Des Plaines, Ill., was calcined at 650° C. for 16 hours in air, pelletized, and sieved to produce 30×60 US mesh sized particles. The catalyst particles were loaded into a 4 mm diameter quartz reactor tube without further treatment. The quartz reactor tube was loaded into an electrically heated zone in the carrier gas stream of an HP 5890 gas chromatograph. Pressure was maintained at 25 psig (273 kPa) for the experiment. Pulses of 1-butene, 1-butene+ methanol and pure methanol were alternatingly passed through the catalyst bed, products were analyzed on-line using a Flame Ionization Detector. Feed consisted of alternating pulses of 1 µl of methanol, 1 ml of 1-butene+1 µl methanol, or 1 ml of 1-butene, respectively. Conversions were calculated based on water and coke free hydrocarbon production in the methanol feed case, and on water, coke and $C_4$ free hydrocarbon production in both the 1-butene alone and 1-butene plus methanol cases. The following were the results, in weight percent selectivity:

| Feed | Conversion | $CH_4$ | $C_2^-$ | $C_3^-$ | $C_4^-$ | $C_5^+$ |
| --- | --- | --- | --- | --- | --- | --- |
| 1-butene | 34.23 | 0.10 | 10.57 | 66.29 | N/A | 21.74 |
| MeOH | 100 | 0.86 | 51.06 | 34.19 | 9.29 | 2.08 |
| MeOH + 1-butene | 84.32 | 1.09 | 45.72 | 41.46 | N/A | 2.67 |

The foregoing results establish that the reaction of butene over an oxygenate-to-olefin catalyst produces propylene, ethylene, and $C_5^+$ hydrocarbons. Additionally, these tests establish that, if both methanol and 1-butene are fed over an oxygenate-to-olefins catalyst, results intermediate between the results for methanol and 1-butene alone are achieved.

EXAMPLE II

The procedures of Example I were repeated except that only 1-butene was used as the feedstock in the process, and two catalysts were used. The first catalyst was SAPO-34 obtained from UOP. The second catalyst was silicalite bound ZSM-5. The results were as follows, in weight percent selectivity:

| Catalyst | Conversion | $CH_4$ | $C_2^-$ | $C_3^-$ | $C_4^-$ | $C_5^+$ |
| --- | --- | --- | --- | --- | --- | --- |
| SAPO-34 | 34.23 | 0.10 | 10.57 | 66.29 | N/A | 21.74 |
| ZSM-5 | 73.10 | 0.21 | 22.31 | 53.03 | N/A | 19.91 |

The foregoing demonstrates that both SAPO-34 and ZSM-5 convert 1-butene to ethylene and propylene, ZSM-5 having a higher overall conversion rate.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

I claim:

1. A method of increasing ethylene yield during conversion of oxygenates to olefins comprising:
   (a) contacting a feed including an oxygenate in a primary reactor with a small pore non-zeolitic molecular sieve catalyst under first conditions effective to produce a first product including ethylene and a heavy hydrocarbon fraction including heavy hydrocarbons;
   (b) separating the ethylene from the heavy hydrocarbon fraction;
   (c) feeding at least a portion of said heavy hydrocarbon fraction to said primary reactor; and
   (d) subjecting said portion of said heavy hydrocarbon fraction in said primary reactor to second conditions effective to convert at least a portion of said heavy hydrocarbons to ethylene.

2. The method of claim 1 wherein said primary reactor contains zeolite molecular sieve catalyst.

3. The method of claim 2 wherein said zeolite is ZSM-5.

4. The method of claim 1 wherein said non-zeolitic molecular sieve catalyst is a silicoaluminophosphate selected from the group consisting of SAPO-44, SAPO-34, SAPO-18, and SAPO-17.

5. The method of claim 1 wherein said non-zeolitic molecular sieve catalyst comprises a microporous framework including pores having a diameter less than about 5 Angstroms.

6. The method of claim 1, wherein the second conditions are the same as the first conditions.

7. The method of claim 1, wherein the primary reactor has a WHSV of at least about 0.01 $hr^{-1}$.

8. The method of claim 7, wherein the WHSV is from about 0.01 $hr^{-1}$ to about 5000 $hr^{-1}$.

9. The method of claim 7, wherein the WHSV is at least about 1.0 $hr^{-1}$.

10. The method of claim 9, wherein the WHSV is from about 1.0 to about 2000 $hr^{-1}$.

11. The method of claim 7, wherein the WHSV is at least about 20 $hr^{-1}$.

12. The method of claim 11, wherein the WHSV is from about 20 $hr^{-1}$ to about 2000 $hr^{-1}$.

13. The method of claim 1, wherein the first conditions include a temperature of from about 200° C. to about 700° C.

14. The method of claim 13, wherein the temperature is from about 250° C. to about 600° C.

15. The method of claim 14, wherein the temperature is from about 300° C. to about 500° C.

16. The method of claim 1, wherein the feed has an oxygenate partial pressure of from about 0.1 kPa to about 100 MPa.

17. The method of claim 16, wherein the oxygenate partial pressure is from about 6.9 to about 34 MPa.

18. The method of claim 17, wherein the oxygenate partial pressure is from about 48 kPa to about 0.3 MPa.

19. A method for increasing ethylene yield during conversion of oxygenates to olefins comprising:
   (a) contacting a feed including an oxygenate in a primary reactor with a small pore non-zeolitic molecular sieve catalyst under conditions effective to produce a product including ethylene;
   (b) separating said product into a product fraction containing the ethylene and a heavy hydrocarbon fraction including heavy hydrocarbons; and
   (c) recycling at least a portion of said heavy hydrocarbon fraction to said primary reactor.

20. The method of claim 19 wherein said non-zeolitic molecular sieve catalyst is SAPO-34.

21. The method of claim 19 further comprising contacting at least a portion of said heavy hydrocarbon fraction with second molecular sieve catalyst in a second reactor to convert a portion of said heavy hydrocarbons to ethylene and propylene.

22. The method of claim 21 wherein said second molecular sieve catalyst is a zeolite.

23. The method of claim 22 wherein said second molecular sieve catalyst is ZSM-5.

24. The method of claim 19 wherein said non-zeolitic molecular sieve catalyst is a silicoaluminophosphate selected from the group consisting of SAPO-44, SAPO-34, SAPO-18, and SAPO-17.

25. The method of claim 19, wherein the primary reactor has a WHSV of at least about 0.01 $hr^{-1}$.

26. The method of claim 25, wherein the WHSV is from about 0.01 $hr^{-1}$ to about 5000 $hr^{-1}$.

27. The method of claim 25, wherein the WHSV is at least about 1.0 $hr^{-1}$.

28. The method of claim 27, wherein the WHSV is from about 1.0 to about 2000 $hr^{-1}$.

29. The method of claim 25, wherein the WHSV is at least about 20 $hr^{-1}$.

30. The method of claim 29, wherein the WHSV is from about 20 $hr^{-1}$ to about 1000 $hr^{-1}$.

31. The method of claim 19, wherein the conditions include a temperature of from about 200° C. to about 700° C.

32. The method of claim 31, wherein the temperature is from about 250° C. to about 600° C.

33. The method of claim 32, wherein the temperature is from about 300° C. to about 500° C.

34. The method of claim 19, wherein the feed has an oxygenate partial pressure of from about 0.1 kPa to about 100 MPa.

35. The method of claim 34, wherein the oxygenate partial pressure is from about 6.9 kPa to about 34 MPa.

36. The method of claim 35, wherein the oxygenate partial pressure is from about 48 kPa to about 0.3 MPa.

* * * * *